(12) United States Patent
Marchant et al.

(10) Patent No.: US 9,618,454 B2
(45) Date of Patent: Apr. 11, 2017

(54) METHOD OF IDENTIFYING A MATERIAL

(75) Inventors: Clive Antony Marchant, Billingham (GB); Vincent Brian Croud, Sheffield (GB)

(73) Assignee: JOHNSON MATTHEY PLC, London (GB)

( * ) Notice: Subject to any disclaimer, the term of this patent is extended or adjusted under 35 U.S.C. 154(b) by 190 days.

(21) Appl. No.: 13/880,596

(22) PCT Filed: Oct. 21, 2011

(86) PCT No.: PCT/GB2011/052050
§ 371 (c)(1),
(2), (4) Date: Jul. 8, 2013

(87) PCT Pub. No.: WO2012/052779
PCT Pub. Date: Apr. 26, 2012

(65) Prior Publication Data
US 2013/0271758 A1    Oct. 17, 2013

Related U.S. Application Data

(60) Provisional application No. 61/412,970, filed on Nov. 12, 2010.

(30) Foreign Application Priority Data

Oct. 22, 2010    (GB) ................................. 1017875.4

(51) Int. Cl.
*G01N 21/85*    (2006.01)
*G01N 21/65*    (2006.01)
(Continued)

(52) U.S. Cl.
CPC .............. *G01N 21/65* (2013.01); *B82Y 15/00* (2013.01); *B82Y 30/00* (2013.01); *G01N 21/274* (2013.01);
(Continued)

(58) Field of Classification Search
USPC ........................................................ 356/301
See application file for complete search history.

(56) References Cited

U.S. PATENT DOCUMENTS 2,392,620 A    8/1942    Sparks
4,659,676 A    4/1987    Rhyne, Jr.
(Continued)

FOREIGN PATENT DOCUMENTS

EP           1 992 938 A1    11/2008
WO       WO-01/25758 A1     4/2001
(Continued)

OTHER PUBLICATIONS

März et al., "The implementation of an isotope-edited internal standard for quantification of lowest drug concentrations using surface enhanced Raman spectroscopy (SERS) in a lab on a chip device," *Proc. of SPIE-OSA Biomedical Optics*, vol. 7368, 2009, pp. 73680R-1-7-680R-7.

(Continued)

*Primary Examiner* — Tarifur Chowdhury
*Assistant Examiner* — Omar Nixon
(74) *Attorney, Agent, or Firm* — RatnerPrestia

(57) ABSTRACT

The invention concerns a method of measuring the amount of a particular SERS-active taggant compound in a sample of a material which includes the steps of adding an internal standard containing an isotopically-altered version of said SERS-active taggant compound to the sample, contacting the sample/internal standard mixture with a SERS substrate then subjecting the mixture and SERS substrate to Raman spectroscopy. The concentration of SERS-active taggant compound in the sample is then calculated from the ratio of (i) the Raman spectroscopy detector response to the SERS-active taggant compound to (ii) the Raman spectroscopy detector response to the internal standard.

20 Claims, 4 Drawing Sheets

(51) Int. Cl.
  *B82Y 15/00* (2011.01)
  *B82Y 30/00* (2011.01)
  *G01N 21/27* (2006.01)
  *G01N 33/28* (2006.01)
(52) U.S. Cl.
  CPC ....... *G01N 21/658* (2013.01); *G01N 33/2882* (2013.01)

(56) References Cited

U.S. PATENT DOCUMENTS

| | | | |
|---|---|---|---|
| 4,735,631 | A | 4/1988 | Orelup |
| 5,358,873 | A | 10/1994 | Nowak |
| 6,770,488 | B1 | 8/2004 | Carron et al. |
| 2004/0258617 | A1* | 12/2004 | Weber et al. ............ 424/9.1 |
| 2006/0240572 | A1* | 10/2006 | Carron et al. ........... 436/524 |
| 2007/0165209 | A1* | 7/2007 | Natan et al. ............. 356/71 |
| 2009/0053818 | A1 | 2/2009 | Zhang et al. |
| 2009/0219526 | A1 | 9/2009 | Davisson et al. |
| 2009/0253117 | A1* | 10/2009 | Cerda et al. ............... 435/4 |

FOREIGN PATENT DOCUMENTS

| | | |
|---|---|---|
| WO | WO-2006/037036 A2 | 4/2006 |
| WO | WO-2008/007242 A2 | 1/2008 |
| WO | WO-2008/019161 A2 | 2/2008 |
| WO | WO-2010/057212 A1 | 5/2010 |
| WO | WO 2010/135226 | 11/2010 |
| WO | WO-2010/138914 A1 | 12/2010 |

OTHER PUBLICATIONS

Zhang et al., "Isotope Edited Internal Standard Method for Quantitative Surface-Enhanced Raman Spectroscopy," *Anal. Chem.*, 2005, vol. 77, pp. 3563-3569.

International Search Report dated Jan. 24, 2012, from PCT International Application No. PCT/GB2011/052050.

British Search Report dated Feb. 22, 2011, from British Patent Application No. 1017875.4.

International Preliminary Report on Patentability dated Apr. 23, 2013, from PCT International Application No. PCT/GB2011/052050.

Combined Search and Examination Report for Application GB 1118180.7 dated Jan. 30, 2012.

\* cited by examiner

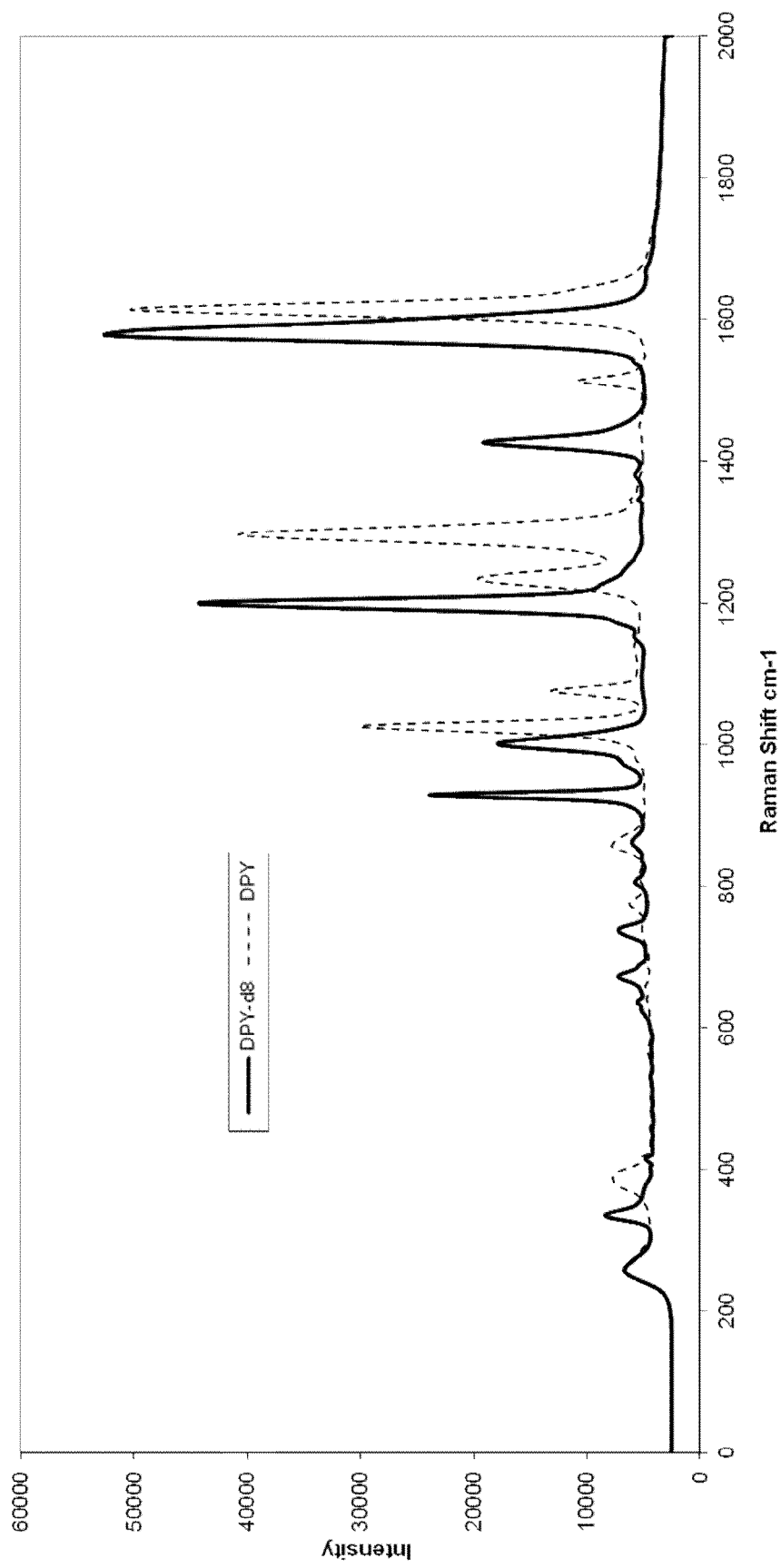

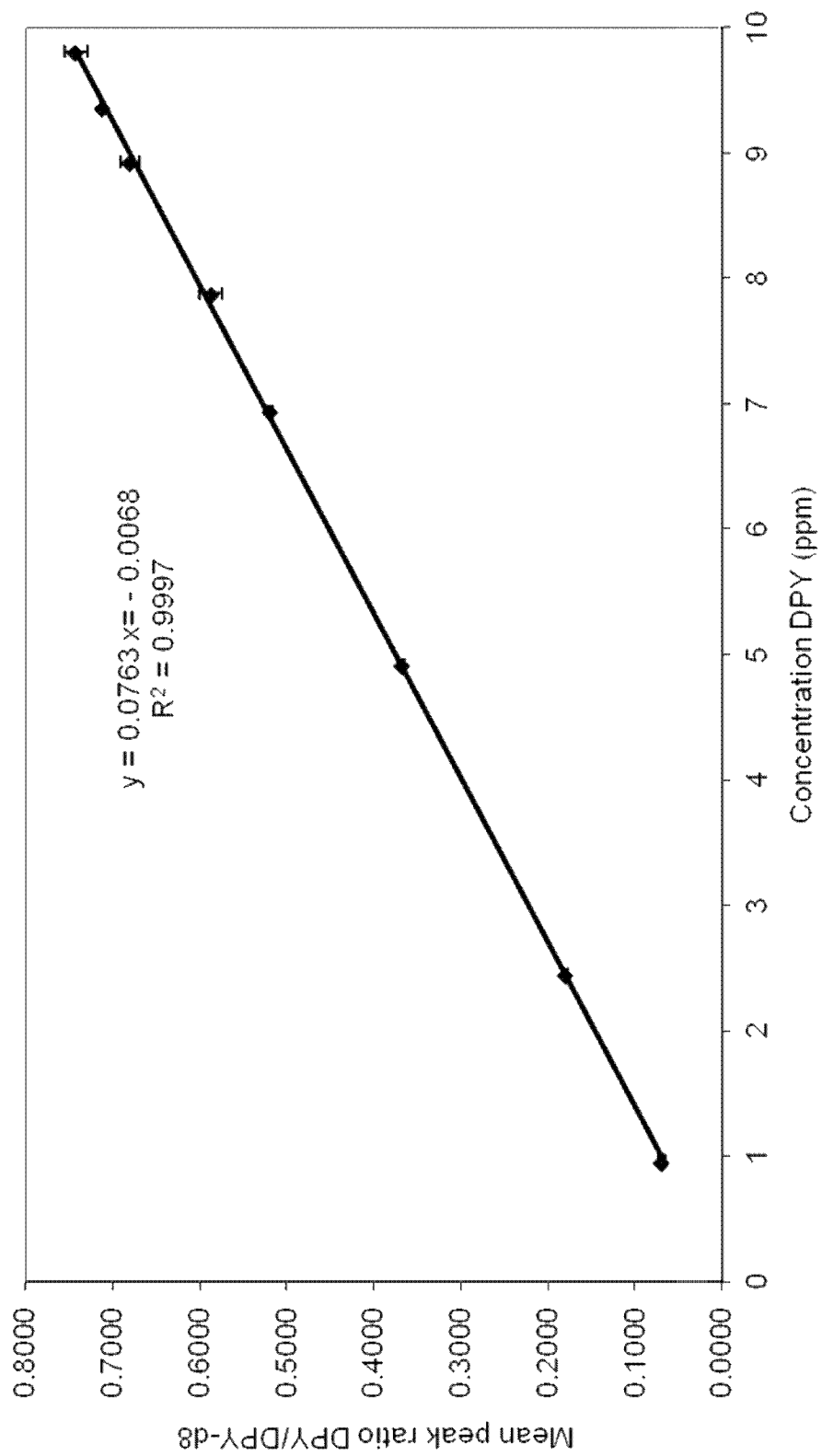

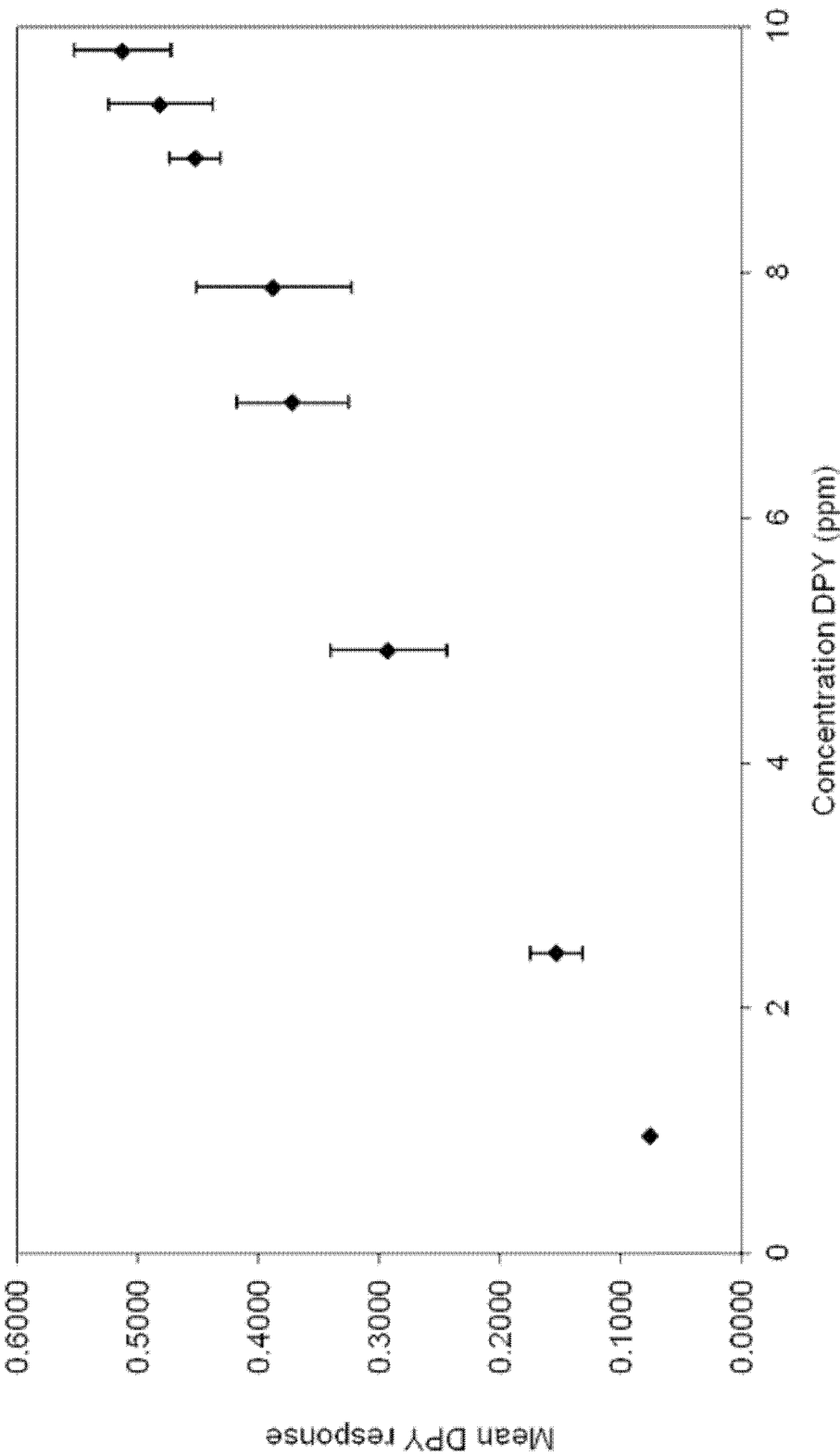

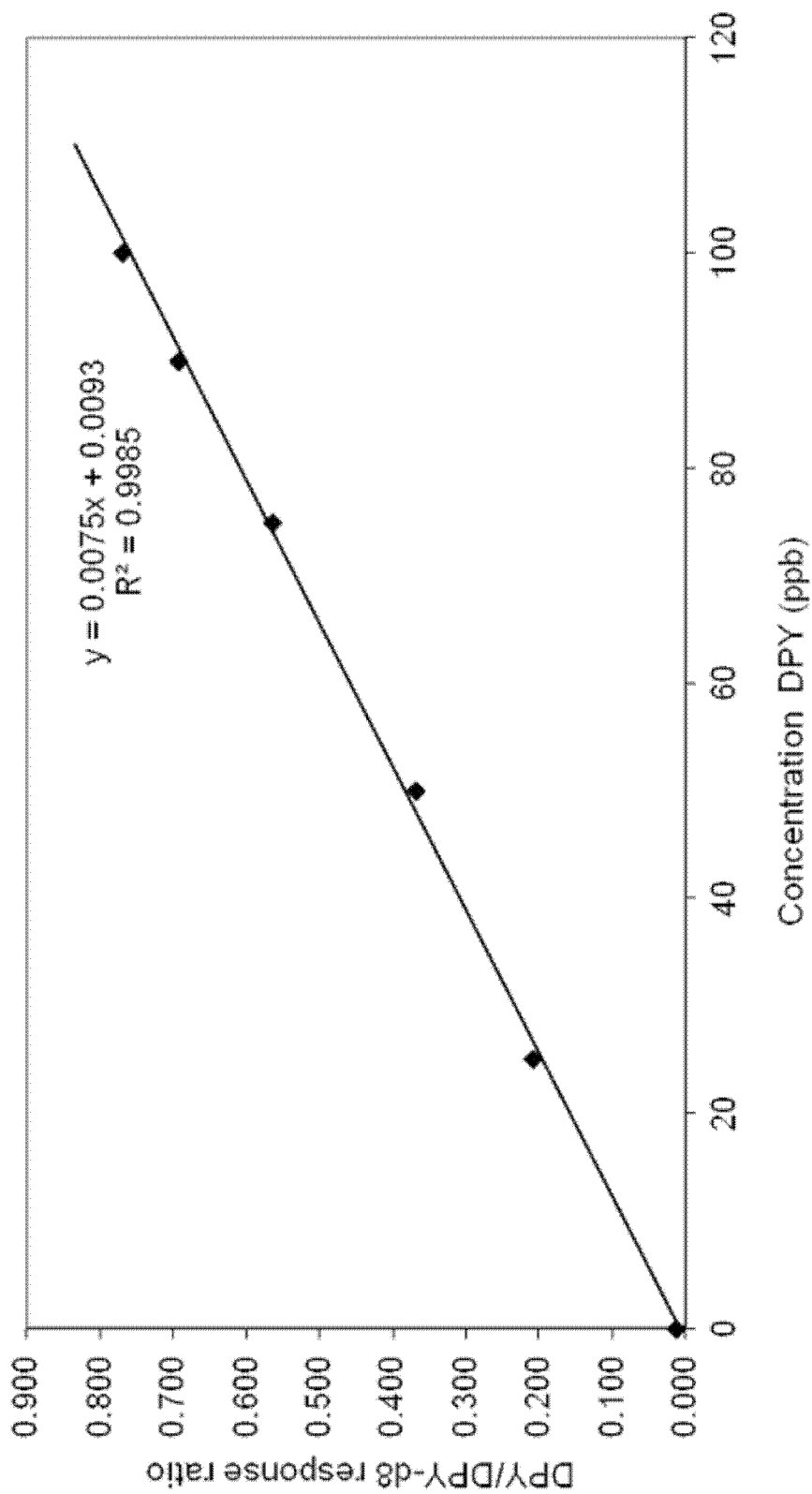

METHOD OF IDENTIFYING A MATERIAL

CROSS-REFERENCE TO RELATED APPLICATIONS

This application is the U.S. National Phase application of PCT International Application No. PCT/GB2011/052050, filed Oct. 21, 2011, and claims priority of British Patent Application No. 1017875.4, filed Oct. 22, 2010, and U.S. Provisional Application No. 61/412,970, filed Nov. 12, 2010, the disclosures of all of which are incorporated herein by reference in their entireties for all purposes.

FIELD OF THE INVENTION

The present invention relates to the analysis of a material to measure the amount of a taggant and identification of a product by adding a known taggant compound to the product and then later analysing a sample of the product or a similar material to determine whether the taggant is present.

BACKGROUND OF THE INVENTION

The use of various compounds as markers or taggants for liquid and solid materials is well known. Fluorescent dyes have been used in many applications, the fluorescence characteristics of a sample of the marked material being used to determine the presence and concentration of the taggant in the material. Other known taggants include biological compounds, especially DNA and oligonucleotides, and also halogenated chemicals such as perfluorocarbons. A typical application of these taggants is in the tagging of liquids such as hydrocarbon fuels in order to identify the liquid at a subsequent point in the supply chain. This may be done for operational reasons, e.g. to assist in distinguishing one grade of fuel from another, or for other reasons, in particular to ensure fuel quality, deter and detect adulteration and to provide a means to check that the correct tax has been paid. Apart from fuels, other products, such as vegetable oils may be marked to identify the product produced at a particular source, which may be licensed to produce or certified to a particular standard.

A problem with the method of detecting fluorescent compounds used as markers arises when the material which is marked interferes with the fluorescence of the marker, by absorbing the excitation or emitted light, by exhibiting its own background fluorescence, or by changing the fluorescent characteristics of the marker. This is a particular problem in the marking of coloured liquids such as petroleum derived products with fluorescent dyes because hydrocarbon based liquids, such as fuels, exhibit a broad fluorescent emission. The fluorescent background tends to add to any fluorescent signal of the dye but the inherent absorbance of the liquid diminishes the fluorescence of the dye. The marking of such fuels, especially gasoline and diesel, is an important use of marker compounds and the ability to detect single or multiple marker compounds with a high degree of certainty is critical to the use of such markers in such valuable and widespread products. The problem has been addressed in many ways, most of which involve the separation of the marker compound from the liquid by means of extraction into a polar liquid or onto a solid absorbent. For example, U.S. Pat. No. 5,358,873 describes and claims a method of detecting gasoline adulteration by tagging with a rhodamine dye and then shaking a small sample of the suspected fuel in a vial containing a small quantity of un-bonded flash chromatography-grade silica. The presence of the rhodamine marker dye in the suspect sample colours the silica red. U.S. Pat. No. 4,659,676 describes a fluorescently labelled complex hydrophobic fluid produced by dissolving therein a porphyrin. The fluorescently labelled complex hydrophobic fluid is identified by observation of the characteristic fluorescence upon irradiation. For identification purposes the porphyrin may be first extracted into an acidic aqueous solution for determination of fluorescence. U.S. Pat. No. 2,392,620 describes the use of umbelliferone or a derivative as a fluorescent marker for petroleum with detection by determination of the characteristic fluorescence after extraction into an aqueous alkaline solution. In U.S. Pat. No. 4,735,631, fuels are marked with certain substituted anthraquinones which are subsequently detected in a marked sample of fuel by extraction into an immiscible alkaline reagent.

Although DNA has been described for use as a taggant for hydrocarbon fuels, the quantitative detection of nucleic acids, for example using hybridisation or quantitative PCR methods, is not sufficiently reproducible to encourage its use as a marker for fuels, where detection of dilution or adulteration of the fuel by detection of relatively small differences in the concentration of the taggant is required.

WO2008/019161 describes a method of fuel identification with surface enhanced Raman spectroscopy (SERS) tags. This method includes the association of a substance having a known Raman spectrum with a quantity of fuel. In one embodiment, a nanoparticle including a SERS active core may be mixed into a fuel supply. In an alternative embodiment, a SERS active dye including a Raman active reporter molecule may be mixed with a quantity of fuel. If the quantity of fuel is tagged with a dye having Raman active reporter molecules, the process of identifying the quantity of fuel may include mixing into a sample of the fuel a colloid of Raman enhancing metal particles and then acquiring the Raman spectrum of the Raman active reporter molecule associated with the tag. Suitable metals include, but are not limited to, silver or gold. Alternatively, a portion of the sample may be associated with a SERS active substrate. Although a semi-quantitative example of the procedure is described in WO2008/019161, we have found that the SERS response of the tags tend to vary such that the results include a significant uncertainty due to non-reproducibility.

SUMMARY OF THE INVENTION

It is an object of the invention to provide a method for identifying a material using a tagging method which overcomes at least some of the disadvantages of such prior methods.

According to the invention, a method of measuring the amount of a particular SERS-active compound in a sample of a material comprises the steps of:—
  a) adding to said sample an internal standard comprising an isotopically-altered version of said SERS-active taggant compound;
  b) contacting said sample containing said internal standard with a SERS substrate;
  c) subjecting said sample and SERS substrate to Raman spectroscopy; and
  d) calculating the ratio of (i) the Raman spectroscopy detector response to the SERS-active taggant compound to (ii) the Raman spectroscopy detector response to the internal standard.

According to a second aspect of the invention, a method of identifying a material comprises the steps of:— a. adding to a first material a SERS-active taggant compound;
b. subsequently obtaining a sample of a second material which is to be compared with said first material;
c. optionally, dissolving or dispersing said sample in a liquid
d. adding to said sample an internal standard comprising an isotopically-altered version of said SERS-active taggant compound;
e. contacting said sample containing said internal standard with a SERS substrate;
f. subjecting said sample and SERS substrate to Raman spectroscopy; and
g. calculating the concentration of said SERS-active taggant compound in said sample from the ratio of (i) the Raman spectroscopy detector response to the SERS-active taggant compound to (ii) the Raman spectroscopy detector response to the internal standard;
h. comparing said calculated concentration with the concentration of SERS-active taggant compound in said first material to determine the similarity of the sample to said first material.

According to a third aspect of the invention, we provide a method of comparing a material to a reference material comprising the steps of:—
a. obtaining a sample of said material;
b. optionally, dissolving or dispersing said sample in a liquid;
c. adding to said sample an internal standard comprising an isotopically-altered version of said SERS-active taggant compound;
d. contacting said sample containing said internal standard with a SERS substrate;
e. subjecting said sample and SERS substrate to Raman spectroscopy; and
f. calculating the ratio of (i) the Raman spectroscopy detector response to the SERS-active taggant compound to (ii) the Raman spectroscopy detector response to the internal standard.
g. comparing the ratio of (i) the Raman spectroscopy detector response to the SERS-active taggant compound to (ii) the Raman spectroscopy detector response to the internal standard with a reference value representing the ratio of (iii) the Raman spectroscopy detector response to the SERS-active taggant compound to (iv) the Raman spectroscopy detector response to the internal standard measured in a sample of said reference material containing a known concentration of SERS-active taggant compound.

According to a fourth aspect of the invention, we provide a method of marking a first material and subsequently identifying whether a sample of a second material is a sample of said marked first material comprising the steps of adding to said first material a SERS-active taggant compound and later
a. obtaining a sample of said second material;
b. optionally, dissolving or dispersing said sample in a liquid;
c. adding to said sample an internal standard comprising an isotopically-altered version of said SERS-active taggant compound;
d. contacting said sample containing said internal standard with a SERS substrate;
e. subjecting said sample and SERS substrate to Raman spectroscopy; and
f. calculating the ratio of (i) the Raman spectroscopy detector response to the SERS-active taggant compound to (ii) the Raman spectroscopy detector response to the internal standard.
g. comparing the ratio of (i) the Raman spectroscopy detector response to the SERS-active taggant compound to (ii) the Raman spectroscopy detector response to the internal standard with a reference value representing the ratio of (iii) the Raman spectroscopy detector response to the SERS-active taggant compound to (iv) the Raman spectroscopy detector response to the internal standard measured in a sample of said reference material containing a known concentration of SERS-active taggant compound;

the concentration of the SERS-active taggant compound in the reference material preferably being the same as or having a known relationship to the concentration of SERS-active taggant compound in the marked first material. The reference material may be a sample of the first material.

BRIEF DESCRIPTION OF THE DRAWINGS

FIG. 1: Raman spectra obtained from dipyridine (DPY) and deuterated dipyridine (DPY-d8).
FIG. 2: Graph of ratio DPY to DPY-d8 vs. DPY concentration (Example 1).
FIG. 3: Graph of mean of the reference peak of the DPY vs. DPY concentration (Example 1).
FIG. 4: Graph of ratio DPY to DPY-d8 vs. DPY concentration (Example 2).

DETAILED DESCRIPTION OF THE INVENTION

The method is suitable for identifying a variety of types of materials, including organic liquids, water, aqueous solutions, powdered solids, particulate solids, solid objects or a plurality of objects. Examples of materials for which the method of the invention may be desirably practised, include hydrocarbons, fuels, mineral oils, vegetable oils, liquids that are known to be used to adulterate fuels and oils such as organic solvents, alcohols, pharmaceuticals, agrochemicals, cosmetics, perfumes and other high value or highly-taxed products. The method has been found to be particularly applicable to identifying hydrocarbon fuels by marking the fuels with a taggant and then measuring the concentration of taggant in a sample of fuel to determine whether the sample is a sample of the marked fuel and also whether the fuel has been diluted with an unmarked or differently marked liquid. The material may be dissolved or dispersed in a liquid before analysis if required. This is especially useful if the material is a solid but may also be used for liquid or semi-liquid materials.

A taggant, as referred to in this specification, is a compound present in a material by means of which the material may be identified. Thus, if a known amount of taggant compound is added to a material before the material is distributed, to form a marked or tagged material, a sample of the distributed material may be identified by analysing the material to determine the presence, absence or the concentration of the taggant compound and comparison with the concentration of taggant in the material before distribution. Adulteration of the distributed material, for example by dilution with an un-tagged material, may also be detected by comparison of the concentration of taggant in the material before and after distribution.

When we refer to SERS in the present specification we intend to include other forms of surface enhanced spectroscopy (SES) such as SERRS (surface-enhanced resonance Raman spectroscopy). For brevity these methods will all be referred to as SERS.

The SERS-active taggant compound is a chemical compound which can be identified by its Raman signal when in contact with a SERS substrate. Suitable taggants are therefore capable of adsorption to a SERS substrate in order that they exhibit surface-enhanced Raman scattering. Suitable taggants produce an enhanced Raman signal when in contact with a SERS substrate compared with the Raman signal produced in the absence of a SERS substrate. When the material to be marked is a liquid, the taggant is preferably soluble in the liquid which is to be marked with the taggant up to the concentration which is to be used. For use in hydrocarbon liquids such as fuels, the taggant is preferably soluble in the fuel up to a concentration which is measurable using SERS analysis. The taggant may be less soluble in the material to be marked than it is in a solvent used to extract the taggant prior to SERS analysis. When the SERS substrate is an aqueous solution of a metal colloid, the taggant may be capable of adsorbing onto the metal surface whilst maintaining the ability of the colloidal particles to partition into the aqueous phase after mixing with the sample. The choice of taggant must therefore take into consideration its capability of producing an enhanced Raman signal through use of SERS methods, its affinity to a SERS substrate surface, and solubility and partitioning properties. The taggant must also be available as an isotopically-altered version for use as an internal standard in the method. Methods of producing isotopically altered molecules are well known and typically include replacing at least one hydrogen atom in the taggant molecule with deuterium or replacing a carbon atom with $C^{13}$. The isotopically altered version of the SERS-active taggant must itself be SERS-active and must produce a SERS Raman signal which is resolvable from the signal produced by the taggant.

The SERS substrate is a substrate having a surface which is capable of enhancing the spectroscopic response of a molecule which is close to or in contact with the surface, i.e. it is capable of promoting surface-enhanced spectroscopy (SES). The SERS substrate may be any material showing surface plasmon enhancement. SERS substrates typically comprise metals such as silver, gold and copper. The use of other SERS substrates, particularly metals, may be possible, including Na and Al and transition metals such as Pt, Ni, Ru, Rh, Pd, Co, Fe, Cr. As new methods of surface-enhanced spectroscopy are developed, different SES-promoting substrates may become available and may be useful for the method of the invention. The SERS substrate may take the form of small particles, usually nanoparticles, typically used as colloidal solutions, especially aqueous colloidal solutions. Alternatively the SERS substrate may take the form of a planar material having a metallic surface comprising microstructure in the form of an immobilised metal colloid or a patterned surface made from or coated with a metal such as gold, silver or copper. Suitable SERS substrates are widely available commercially, either as colloidal gold or silver solutions or as specialist planar materials for SERS having plasmonic surfaces, such as Klarite™.

The SERS-active taggant compound and/or the internal standard may be incorporated in a "nanotag" including a SERS substrate. Suitable nanotags include SERS-active composite nanoparticles which are described, for example, in WO01/25758 and comprise a SES (surface enhanced spectroscopy) metal nanoparticle, a layer of a SES-active species in close proximity to the metal surface and an encapsulating shell comprising a polymer, glass or another dielectric material. The internal standard may comprise a nanotag incorporating an isotopically-altered version of the SERS-active taggant compound. For example, the internal standard may comprise a SES metal nanoparticle, a layer of a SES-active species in close proximity to the metal surface and an encapsulating shell comprising a polymer, glass or another dielectric material in which the SES-active species is an isotopically-altered version of the SERS-active taggant compound.

The taggant is added to the material to be marked by standard means, for example when the material is held in bulk volumes at a manufacturing or distribution location. Different taggants may be added to different volumes of material of the same bulk composition which are intended for different purposes or for use in different territories or which originate from different batches of material. Alternatively, different taggants may be added to different bulk volumes of material having different compositions, for example to distinguish between fuels of different grades. The concentration of taggant in the material is preferably in the range from 1 ppb (i.e. 0.001 ppm) to 100 ppm, more preferably from 10 ppb to 10 ppm. The taggant is normally added to the material in amounts less than 10 ppm. "ppb" means parts per billion. "ppm" means parts per million. More than one taggant may be added to a single material and the use of combinations of different taggants in varying relative amounts may provide a large number of uniquely tagged materials using relatively few taggant compounds.

The taggant may be added to a component of the material to be marked. For example, when the material is an agrochemical, the taggant may be added to one ingredient of the composition, such as a dispersing agent, for example. When the material to be marked is a fuel then the taggant may be added to a fuel additive which is then incorporated into the bulk fuel before it is distributed. In these cases, the material becomes marked with the taggant when the ingredient incorporating the taggant is added to the material composition during preparation or manufacture. Alternatively the taggant may be added to or mixed with a solvent before it is mixed with the material to be marked.

When it is required to determine the amount of a particular SERS-active taggant in a sample of a material the method of the invention is used. When analysing for a SERS-active compound in an organic liquid sample by a standard prior art SERS method using an aqueous gold colloid, we have found that the variation in results between identical samples, possibly caused by unpredictable variation in the colloidal gold and the aggregation behaviour of the gold nanoparticles, can be very large, giving a relative standard deviation of about 20%. This variation is unacceptable for detecting fuel adulteration by dilution because the difference between the amount of taggant detected in the sample and that added to the original liquid is used to indicate the presence of an untagged liquid.

The use of internal standards in analytical methods is widely practised. The relative response of the target compound and internal standard to the analytical technique is likely to be insensitive to inconsistencies in carrying out the method or in the nature of the sample and so using an internal standard can reduce the error in the analysis caused by such factors. Use of an internal standard can overcome the error in analysing for a SERS active taggant in fuel because the relative response of the internal standard and the taggant should be dependent only on the relative concentration of the internal standard and the taggant. However, SERS is very dependent on the adsorption of the SERS active compound to the SERS substrate, aggregation of the gold particles to which they have adsorbed and, in the case of analysis of organic liquids, on the partitioning of the SERS active compound and the gold nanoparticles between organic and aqueous phases. For that reason the internal standard must be as chemically similar to the SERS-active taggant compound as possible, so that it behaves in the same way. The internal standard used in the present method is therefore an isotopically altered (or "isotopically edited") version of the taggant compound. The concentration of internal standard added to the sample may be greater or less than the concentration of SERS-active taggant expected to be present in the sample. The concentration of internal standard added to the sample is preferably in the range from 1 ppb (i.e. 0.001 ppm) to 100 ppm, more preferably from 10 ppb to 10 ppm. Normally the concentration of internal standard added to the sample is the same as the concentration of internal standard in the reference sample.

The amount of sample used for analysis by the method of the invention must be accurately known. Suitable methods of sampling are known and may involve the use of volumetric flasks or a sampling loop. The internal standard is added to the sample in an accurately known quantity and mixed thoroughly.

The sample may be diluted with a suitable solvent or with a further volume of the liquid comprising the bulk of the sample. In the case of analysis of hydrocarbon liquid samples, especially fuel samples, we have found that it may be useful to mix the sample with a non-polar solvent, such as an alkane, for example iso-octane, n-octane, decane or dodecane. The volume ratio of sample to solvent used is typically in the range 1:1-50. The use of a solvent may enhance the partitioning of the taggant and metal nanoparticles into an aqueous phase. We believe that this is because the more non-polar the sample becomes through dilution, the greater is the likelihood of partitioning of a moderately polar taggant molecule, attached to a colloidal gold particle, into the aqueous phase. When a solvent is used, it is preferably added to the sample before the sample is contacted with the SERS substrate. It is further preferred to add the internal standard to the sample before adding a solvent.

When the SERS substrate is a metal colloid in solution, the contact of the SERS-active taggant compound and the internal standard in the sample with the SERS substrate is carried out by mixing, e.g. by shaking, the colloid solution with the sample for sufficient time to allow the molecules in the sample to adsorb on the metal surfaces. The time allowed for this mixing should be kept constant between samples. When the mixture is allowed to settle, the colloidal metal particles partition into the aqueous phase. The metal particles carrying the adsorbed SERS-active molecules normally form aggregates. The sample and SERS substrate is then subjected to Raman spectroscopy to obtain the Raman spectrum of the aqueous portion of the mixture using known methods.

It is normally beneficial for the colloidal metal particles to form aggregates comprising several particles in the presence of the SERS-active taggant compound. Aggregation may take place spontaneously, depending on the nature of the colloid and the compounds present in the mixture to be analysed. As an option, one or more aggregating agents may be used in order to improve the aggregation of the colloidal metal particles in the presence of the SERS-active taggant compound. Suitable aggregating agents may be selected according to the nature of the colloidal metal and/or the SERS-active taggant compound. Known aggregating agents which may be useful include compounds which affect the ionic concentration in the colloid, such as active or passive salts, acids and bases; polymers or long-chain ions which may affect the surface charge of the colloid or otherwise alter the colloidal properties e.g. by affecting steric interaction or stability of the colloid by displacement of or interaction with colloidal stabilisers. Typical examples of aggregating agents include sodium chloride, sodium sulphate, sodium nitrate, potassium nitrate, potassium chloride, calcium chloride, nitric acid, sulphuric acid, sulphurous acid, hydrochloric acid, spermine, and poly(L)lysine.

The relative amount of the SERS-active taggant compound and the internal standard may be calculated from the ratio of (i) the Raman spectroscopy detector response to the SERS-active taggant compound to (ii) the Raman spectroscopy detector response to the internal standard. The detector response ratio may be the ratio of selected peaks (peak height, peak area) of the SERS spectrum. Preferably the concentration of said SERS-active taggant compound in said sample is calculated from the ratio calculated in step (d) of the method. The ratio calculated in step (d) is preferably compared with a reference value representing the ratio of (i) the Raman spectroscopy detector response to the SERS-active taggant compound to (ii) the Raman spectroscopy detector response to the internal standard from a reference sample containing a known concentration of SERS-active taggant compound. The SERS spectrum obtained from a reference sample containing only the target SERS-active taggant or the internal standard may be used to identify suitable peaks which are characteristic of either the taggant or the internal standard, which may be selected for comparing the relative response of the compounds. The relative response may be calculated from the relative intensity of one peak attributable to each compound or from more than one peak. As an alternative, the whole spectrum, or a portion of it, obtained from the Raman spectroscopy of the sample in contact with the SERS substrate may be compared, preferably in vector form, to a spectrum obtained from a reference sample containing a known concentration the SERS-active taggant compound in contact with the SERS substrate and a spectrum obtained from a reference sample containing a known concentration the internal standard compound in contact with the SERS substrate. A calculated property of the spectrum, such as the relative response compared to a reference spectrum of one or each compound present, may be used to represent the detector response due to the SERS-active taggant and/or the internal standard. It is not always necessary to collect and display a Raman spectrum. Since the identity of the taggant and internal standard are known, it may be sufficient to measure the detector response at one or more predetermined Raman shift wavenumbers or ranges of wavenumbers and calculate a concentration of the taggant from the measured response. The result of the calculation may be displayed to the user as a concentration value, a "pass/fail" result or as an arbitrary value of quality or similarity based upon a value for a solution containing a standard amount of the taggant. Methods of comparing spectra and calculating relative response and peak ratios are well-known and are typically carried out using a suitable computer programmed with spectroscopic data handling software. The relationship between the concentration of the SERS-active taggant compound and the Raman detector response ratio is linear and may be determined by calibration.

The analysis of the detector responses may be carried out using the following method, in which we assume that the spectrum to be analysed comes from a mixture of known SERS active components. From the physics of Raman spectroscopy, the analysed spectrum of a mixed solution is, at least approximately, a weighted linear combination of the pure spectra, i.e. the taggant and the internal standard. Therefore, by treating the spectra as vectors we can represent this algebraically as:

$$S = w(\text{taggant})C(\text{taggant}) + w(\text{internal standard})C(\text{internal standard}) + R$$

where:
S=Captured Spectrum of the Sample
C=Reference Spectrum for each Component
w=weight assigned to each component
R=the Residual (In ideal mixture analysis, R will be noise and therefore tend to zero).

The weight assignment of each component within the recorded SERS spectrum of the mixture is calculated and recorded. If the same amount of internal standard is added to each of the samples, the concentration of the internal standard in each sample should be the same, within experimental error of the addition. The measured amount of internal standard found in the samples is then indicated by the intensity of the weight assignment computed against the stored internal standard reference spectra. This could also be expressed as:

$$\frac{[TAGGANT]}{[\text{Internal standard}]} \propto \frac{S_{TAGGANT}/C_{TAGGANT}}{S_{Internal\ standard}/C_{Internal\ standard}}$$

A preferred embodiment of the method of the invention is a method for determining the amount of a SERS-active taggant compound in a sample of a liquid hydrocarbon, comprising the steps of:—mixing the sample with a quantity of a non-polar solvent; adding an internal standard comprising an isotopically-altered version of said SERS-active taggant compound to the mixture;
contacting said mixture containing said internal standard with a SERS substrate;
subjecting the mixture and SERS substrate to Raman spectroscopy; and
calculating the concentration of said SERS-active taggant compound in said sample from the ratio of (i) the Raman spectroscopy detector response to the SERS-active taggant compound to (ii) the Raman spectroscopy detector response to the internal standard.

EXAMPLES

The method of the invention will be demonstrated in the following illustrative examples, with reference to the drawings:—

The taggant used in the examples is dipyridine (DPY). The internal standard is deuterated dipyridine (DPY-d8). FIG. 1 shows that the Raman spectra obtained from DPY (dashed line) and DPY-d8 (solid line) are resolvable and show a similar pattern of peaks but at a relative Raman shift of approximately 100 $cm^{-1}$.

Example 1

Mixtures of DPY in kerosene were prepared at different concentrations between about 10 ppm and 1 ppm as shown in Table 1. Each mixture was analysed by the method of the invention by the following method.
  i. 5 mls of the mixture was measured accurately into a 5 ml grade A volumetric flask.
  ii. 50 µl of 1000 ppm DPY-d8 internal standard in kerosene was accurately dispensed, using a micropipette, and the resulting solution thoroughly mixed.
  iii. 100 µl of the resulting mixed solution was dispensed into a glass 2 ml vial, 400 µl of solvent (iso-octane) was added and the resulting solution mixed.
  iv. To this resulting solution 500 µl of SERS colloid (aqueous citrate-stabilised 90 nm gold colloid), containing 0.5 mg/ml of gold, was dispensed and mixed for 30 seconds. Some aggregation of the colloidal gold particles was indicated by a slight colour change from red towards purple.
  v. Within about 20 seconds of the two phases separating, the aqueous phase was analysed on an Ocean Optics™ QE-RAMAN-785 scientific grade Raman spectrometer, coupled to an Innovative Photonic Solutions™ 350 mW, 785 nm spectrum stabilised laser module (Model No.: I0785MM0350MS), via an InPhotonics RPB785 fibre optic Raman probe.

Reference spectra were recorded for each standard component by measuring a 10 ppm standard of each component using the above method from step iii. Each mixture was sampled and analysed three times and the results are shown in Table 1.

The analysis assumes that the spectrum to be analysed comes from a mixture of known SERS active components. From the physics of Raman spectroscopy, the analysed spectrum of the mixed solution is, at least approximately, a weighted linear combination of the pure spectra (in this case DPY and DPY-d8). Therefore, by treating the spectra as vectors we can represent this algebraically as:

$$S = w(\text{DPY})C(\text{DPY}) + w(\text{DPY-d8})C(\text{DPY-d8}) + R$$

where:
S=Captured Spectrum of the Sample
C=Reference Spectrum for each Component
w=weight assigned to each component
R=the Residual (In ideal mixture analysis, R will be noise and therefore tend to zero).

The weight assignment of each component within the recorded SERS spectrum of the mixture (sample) was calculated and recorded. The same amount of DPY-d8 internal standard was added to each of the samples and so the concentration of the DPY-d8 in each sample should be the same, within experimental error of the addition. The measured amount of DPY-d8 found in the samples is indicated by the intensity of the weight assignment computed against the stored DPY-d8 reference spectra. This could also be expressed as:

$$\frac{[DPY]}{[DPY-d8]} \propto \frac{S_{DPY}/C_{DPY}}{S_{DPY-d8}/C_{DPY-d8}}$$

The mean of Ref peak DPY-d8 for all 24 samples in Table 1 is 0.768 with a standard deviation of 0.160. This gives a calculated reference standard deviation of 20.83%, indicating that a simple comparison of a measured SERS reference peak with a calibration of peak intensity vs concentration for DPY-d8 would produce an error which is not acceptable for determining taggant concentration to detect fuel dilution.

The mean ratio of reference peaks of DPY to DPY-d8 is plotted vs DPY concentration in FIG. 2 together with the error (calculated as +/−2×standard deviations). The relationship between the peak ratio and the concentration of DPY is linear with linear regression properties y=0.0736, x=−0.0068 and $R^2$=0.9997.

The mean of the reference peak of the DPY ("Ref peak DPY") was calculated and plotted vs DPY concentration in FIG. 3 together with the error (calculated as +/−2×standard deviations). The greatly reduced error using the method of the invention is evident by comparing the size of the error bars in FIGS. 2 and 3.

TABLE 1

| DPY Conc. (ppm) | Rep No. | Ref peak DPY | Ref peak DPY-d8 | Ratio DPY/DPY-d8 | Mean ratio | Error |
|---|---|---|---|---|---|---|
| 9.81 | 1 | 0.492 | 0.678 | 0.7257 | 0.7417 | 0.0280 |
|  | 2 | 0.559 | 0.744 | 0.7513 |  |  |
|  | 3 | 0.487 | 0.651 | 0.7481 |  |  |
| 9.37 | 1 | 0.460 | 0.645 | 0.7132 | 0.7119 | 0.0023 |
|  | 2 | 0.531 | 0.747 | 0.7108 |  |  |
|  | 3 | 0.452 | 0.635 | 0.7118 |  |  |
| 8.93 | 1 | 0.469 | 0.681 | 0.6887 | 0.6803 | 0.0215 |
|  | 2 | 0.429 | 0.642 | 0.6682 |  |  |
|  | 3 | 0.459 | 0.671 | 0.6841 |  |  |
| 7.88 | 1 | 0.315 | 0.530 | 0.5943 | 0.5869 | 0.0261 |
|  | 2 | 0.410 | 0.717 | 0.5718 |  |  |
|  | 3 | 0.437 | 0.735 | 0.5946 |  |  |
| 6.94 | 1 | 0.406 | 0.783 | 0.5185 | 0.5180 | 0.0048 |
|  | 2 | 0.319 | 0.619 | 0.5153 |  |  |
|  | 3 | 0.390 | 0.750 | 0.5200 |  |  |
| 4.92 | 1 | 0.237 | 0.649 | 0.3652 | 0.3664 | 0.0027 |
|  | 2 | 0.320 | 0.874 | 0.3661 |  |  |
|  | 3 | 0.320 | 0.870 | 0.3678 |  |  |
| 2.45 | 1 | 0.171 | 0.958 | 0.1785 | 0.1803 | 0.0080 |
|  | 2 | 0.129 | 0.698 | 0.1848 |  |  |
|  | 3 | 0.159 | 0.896 | 0.1775 |  |  |
| 0.96 | 1 | 0.075 | 1.009 | 0.0743 | 0.0697 | 0.0085 |
|  | 2 | 0.078 | 1.183 | 0.0659 |  |  |
|  | 3 | 0.074 | 1.075 | 0.0688 |  |  |

Example 2

The tagged material for this example was a diesel fuel containing a fuel additive pack. In order to calibrate the analysis, six different mixtures of DPY in the diesel fuel were prepared at different concentrations between 0 and 100 ppb as shown in Table 2. Each mixture was analysed as follows:

1000 μl of a sample of the fuel containing the DPY taggant was dispensed using a micro-pipette into a 2 ml vial. 10 μl of 100 ppm DPY-d8 internal standard in iso-octane was accurately dispensed by micro-pipette into the same vial and the resulting solution thoroughly mixed. A 100 μl sample of the mixed solution was dispensed into 500 μl of SERS colloid (aqueous citrate-stabilised 60 nm gold colloid) and mixed until the colour changed from red to purple observed. The aqueous phase was then analysed by Raman spectroscopy using the method and apparatus described in Example 1 using an exposure time of 4 seconds. The results, showing the peak ratios of DPY to DPY-d8 are shown in Table 2 and FIG. 4.

TABLE 2

| Conc. Ppb | DPY Resp. | D8 Resp. | DPY/D8 Ratio |
|---|---|---|---|
| 100 | 0.799 | 1.040 | 0.768 |
| 90 | 0.676 | 0.978 | 0.691 |
| 75 | 0.652 | 1.158 | 0.563 |
| 50 | 0.403 | 1.099 | 0.367 |
| 25 | 0.208 | 1.006 | 0.207 |
| 0 | 0.009 | 0.702 | 0.013 |

Following the calibration, the analysis was repeated 10 times on a fuel sample containing 100 ppb of DPY taggant. The peak response ratios of DPY:DPY-d8 were used, together with the calibration, to calculate the concentration of DPY in the sample. The mean calculated DPY concentration was 99.5 ppb, standard deviation 1.7 and a calculated reference standard deviation of 1.7%. Therefore good precision was achieved for the analysis even though the concentration of taggant in the sample was only 100 ppb.

The invention claimed is:

1. A method of measuring the amount of a particular SERS-active taggant compound in a sample of liquid comprising the steps of:—
    a) adding to said sample an internal standard comprising an isotopically-altered version of said SERS-active taggant compound;
    b) contacting said sample containing said internal standard with a SERS substrate;
    c) subjecting said sample and SERS substrate to Raman spectroscopy; and
    d) calculating the ratio of (i) the Raman spectroscopy detector response to the SERS-active taggant compound to (ii) the Raman spectroscopy detector response to the internal standard.

2. A method according to claim 1, wherein said sample is dissolved or dispersed in a liquid prior to step (b).

3. A method according to claim 1, wherein the SERS substrate comprises silver, gold, or copper.

4. A method according to claim 1, wherein the SERS substrate is in the form of a colloidal solution.

5. A method according to claim 1, wherein the SERS substrate is in the form of a planar material having a metallic surface comprising microstructure.

6. A method according to claim 5, wherein the SERS substrate is an immobilised metal colloid or a patterned surface made from or coated with a metal.

7. A method according to claim 1, wherein a solvent is added to the sample before step (b).

8. A method according to claim 7, wherein the solvent is a non-polar solvent.

9. A method according to claim 1, wherein the concentration of said SERS-active taggant compound in said sample is calculated from the ratio calculated in step (d).

10. A method according to claim 1, wherein the ratio calculated in step (d) is compared with a reference value representing the ratio of (iii) the Raman spectroscopy detector response to the SERS-active taggant compound to (iv) the Raman spectroscopy detector response to the internal standard from a reference sample containing a known concentration of SERS-active taggant compound.

11. A method of comparing a liquid material to a reference liquid material comprising the steps of:—
    a. obtaining a sample of said liquid material;
    b. optionally, dissolving or dispersing said sample in a liquid;
    c. carrying out the method of claim 1;
    d. comparing the ratio of (i) the Raman spectroscopy detector response to the SERS-active taggant compound to (ii) the Raman spectroscopy detector response to the internal standard with a reference value representing the ratio of (iii) the Raman spectroscopy detector response to the SERS-active taggant compound to (iv) the Raman spectroscopy detector response to the internal standard measured in a sample of said reference liquid material containing a known concentration of SERS-active taggant compound.

12. A method of marking a first liquid material and subsequently identifying whether a sample of a second liquid material is a sample of said marked first liquid material comprising the steps of adding to said first liquid material a SERS-active taggant compound and later carrying out the method of claim 11 on said second liquid material.

13. A method according to claim 12, wherein the concentration of the SERS-active taggant compound in the reference liquid material is the same as the concentration of SERS-active taggant compound in the marked first liquid material.

14. A method according to claim 12, wherein more than one taggant compound is added to the first liquid material.

15. A method according to claim 12, wherein said first liquid material is an organic liquid.

16. A method according to claim 11, wherein said liquid material is an organic liquid.

17. A method according to claim 1, wherein the sample of liquid is an organic liquid.

18. A method according to claim 1, wherein said sample of liquid comprises an organic liquid, water, an aqueous solution, a powdered solid, a particulate solid, a solid object, or a plurality of objects.

19. A method according to claim 18, wherein said sample of liquid comprises a hydrocarbon, fuel, mineral oil, vegetable oil, organic solvent, alcohol, pharmaceutical, agrochemical, cosmetic, or perfume.

20. A method for determining the amount of a SERS-active taggant compound in a sample of a liquid hydrocarbon, comprising the steps of:

mixing the sample with a quantity of a non-polar solvent;

adding an internal standard comprising an isotopically-altered version of said SERS-active taggant compound to the mixture;

contacting said mixture containing said internal standard with a SERS substrate;

subjecting the mixture and SERS substrate to Raman spectroscopy; and calculating the concentration of said SERS-active taggant compound in said sample from the ratio of (i) the Raman spectroscopy detector response to the SERS-active taggant compound to (ii) the Raman spectroscopy detector response to the internal standard.

* * * * *